(12) United States Patent
Chu

(10) Patent No.: US 8,702,729 B2
(45) Date of Patent: Apr. 22, 2014

(54) PLACING MULTIPLE SUTURES

(75) Inventor: Michael S. H. Chu, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 933 days.

(21) Appl. No.: 11/869,490

(22) Filed: Oct. 9, 2007

(65) Prior Publication Data

US 2008/0091220 A1    Apr. 17, 2008

Related U.S. Application Data

(60) Provisional application No. 60/851,399, filed on Oct. 13, 2006.

(51) Int. Cl.
*A61B 17/04* (2006.01)
(52) U.S. Cl.
USPC .......................................... 606/144
(58) Field of Classification Search
USPC ................................. 606/144, 139
See application file for complete search history.

(56) References Cited

U.S. PATENT DOCUMENTS

| | | | |
|---|---|---|---|
| 3,090,386 | A | 5/1963 | Curtis |
| 5,364,408 | A | 11/1994 | Gordon |
| 5,374,275 | A * | 12/1994 | Bradley et al. ............ 606/144 |
| 5,454,823 | A | 10/1995 | Richardson et al. |
| 5,458,609 | A | 10/1995 | Gordon et al. |
| 5,474,565 | A | 12/1995 | Trott |
| 5,478,344 | A | 12/1995 | Stone et al. |
| 5,478,345 | A | 12/1995 | Stone et al. |
| 5,540,704 | A | 7/1996 | Gordon et al. |
| 5,575,800 | A | 11/1996 | Gordon |
| 5,578,044 | A | 11/1996 | Gordon et al. |
| 5,662,664 | A | 9/1997 | Gordon et al. |
| 5,700,272 | A | 12/1997 | Gordon et al. |
| 5,713,910 | A | 2/1998 | Gordon et al. |
| 5,741,277 | A | 4/1998 | Gordon et al. |

(Continued)

FOREIGN PATENT DOCUMENTS

WO          9853745 A1     12/1998

OTHER PUBLICATIONS

Notification Concerning Transmittal of International Preliminary Report on Patentability (Chapter I of the Patent Cooperation Treaty), mailed Apr. 23, 2009.

(Continued)

*Primary Examiner* — Gregory Anderson

(57) ABSTRACT

A suturing instrument for placing multiple sutures include an elongate body engaged to a handle. A suturing head extends from a distal end of the elongate body, and the suturing head is articulable relative to the elongate body. Both a first needle carrier and a second needle carrier are movable into and out of the suturing head. A first actuator allows controlled movement of the first needle carrier, and this first actuator extends from a proximal end of the handle. A second actuator allows controlled movement of the second needle carrier, and this second actuator also extends from the proximal end of the handle. The suturing head can be articulated within a range of about 0 degrees to about 30 degrees, as measured from a longitudinal axis running along the length of the elongate body, and this variable articulation angle of the head allows deployment of the first needle carrier and the second needle carrier at various orientations with respect to the longitudinal axis.

15 Claims, 10 Drawing Sheets

(56) References Cited

U.S. PATENT DOCUMENTS

| | | | |
|---|---|---|---|
| 5,741,279 | A | 4/1998 | Gordon et al. |
| 6,048,351 | A | 4/2000 | Gordon et al. |
| 6,096,051 | A | 8/2000 | Kortenbach et al. |
| 6,454,778 | B2 | 9/2002 | Kortenbach |
| 6,506,197 | B1 | 1/2003 | Rollero et al. |
| 6,551,329 | B1 | 4/2003 | Kortenbach et al. |
| 6,936,054 | B2 | 8/2005 | Chu |
| 6,955,643 | B2 * | 10/2005 | Gellman et al. ............ 600/104 |
| 7,041,111 | B2 | 5/2006 | Chu |
| 7,048,749 | B2 | 5/2006 | Kortenbach et al. |
| 7,104,949 | B2 | 9/2006 | Anderson et al. |
| 7,122,039 | B2 | 10/2006 | Chu |
| 8,123,762 | B2 * | 2/2012 | Chu et al. .................... 606/144 |
| 2001/0049537 | A1 | 12/2001 | Kortenbach |
| 2003/0208208 | A1 | 11/2003 | Chu |
| 2004/0002720 | A1 | 1/2004 | Kortenbach et al. |
| 2004/0015177 | A1 | 1/2004 | Chu |
| 2004/0034372 | A1 | 2/2004 | Chu |
| 2004/0059352 | A1 | 3/2004 | Burbank et al. |
| 2004/0181243 | A1 | 9/2004 | Chu et al. |
| 2004/0199246 | A1 | 10/2004 | Chu et al. |
| 2005/0222589 | A1 | 10/2005 | Chu |
| 2006/0004385 | A1 | 1/2006 | Gellman et al. |
| 2006/0041263 | A1 | 2/2006 | Chu et al. |
| 2006/0064115 | A1 | 3/2006 | Allen et al. |
| 2006/0178681 | A1 | 8/2006 | Kortenbach et al. |
| 2006/0184234 | A1 | 8/2006 | Frazier et al. |
| 2006/0195121 | A1 | 8/2006 | Chu |
| 2006/0206119 | A1 | 9/2006 | Chu |
| 2006/0212022 | A1 | 9/2006 | Gellman |
| 2007/0173864 | A1 | 7/2007 | Chu |

OTHER PUBLICATIONS

*Notification of Transmittal of the International Search Report and the Written Opinion of the International Searching Authority, or the Declaration* (Form PCT/ISA/220), together with the International Search Report (Form PCT/ISA/210) and the Written Opinion of the International Searching Authority (Form PCT/ISA/237) dated Apr. 7, 2008 issued in corresponding PCT patent application No. PCT/US07/81078.

EPO Search Opinion from European Patent Application No. 07 844 159.9 (4 pages).

Supplementary European Search Report for European Patent Application No. 07 84 4159, dated Dec. 9, 2011 (4 pages).

* cited by examiner

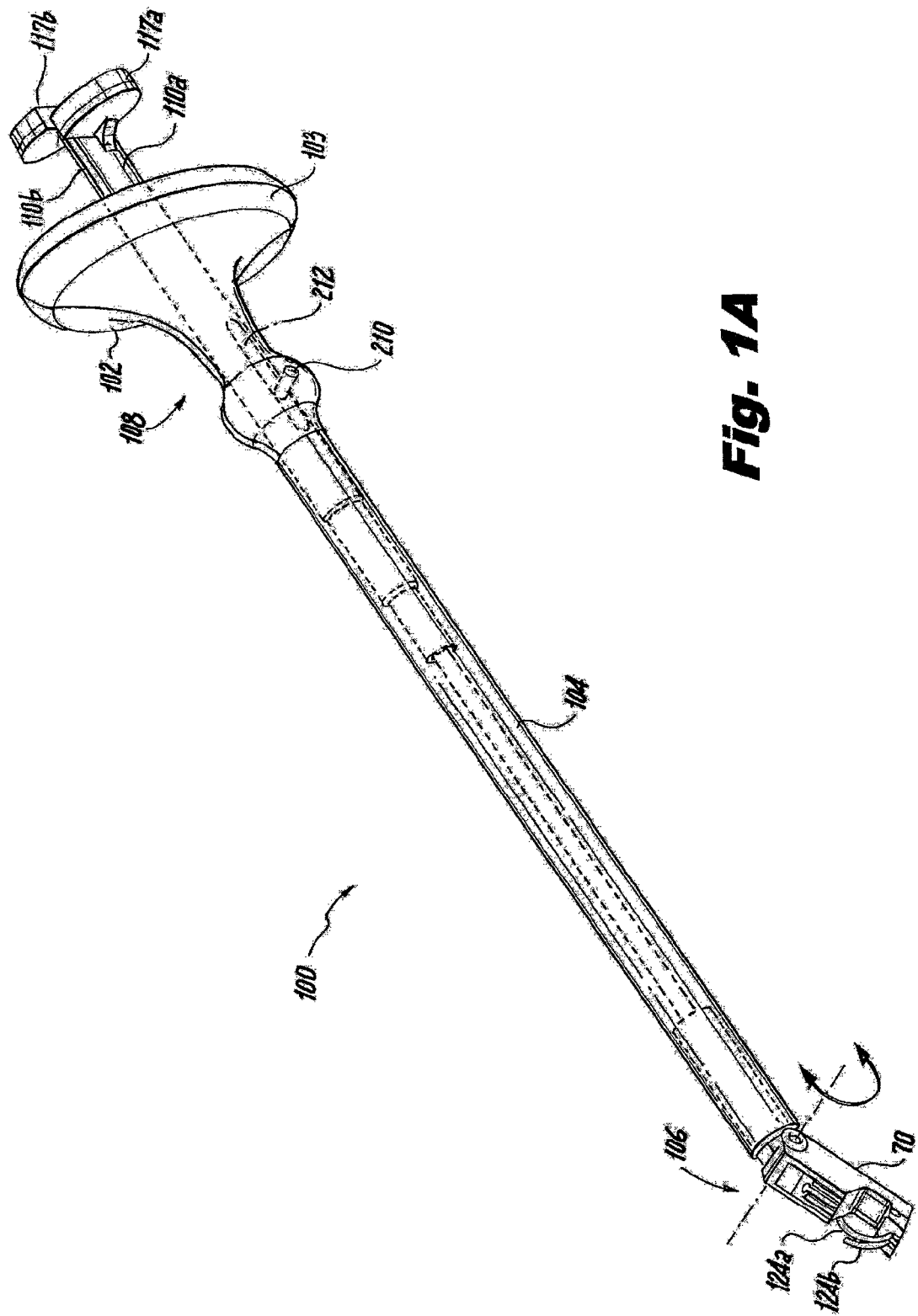

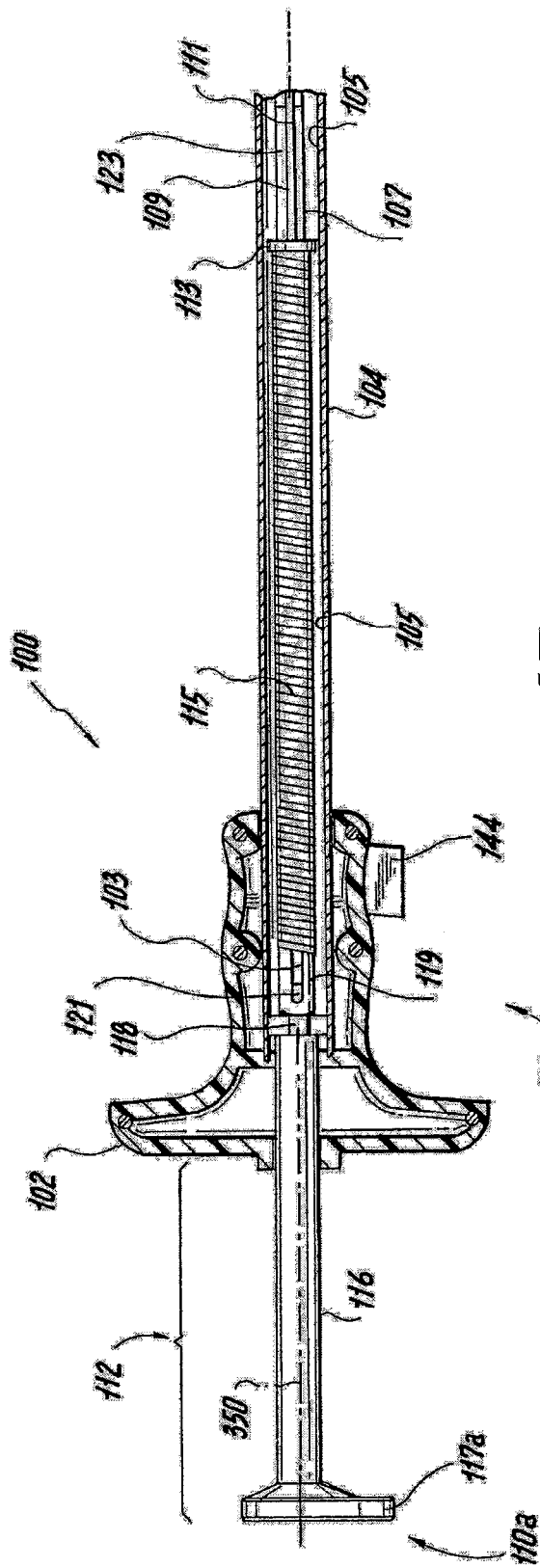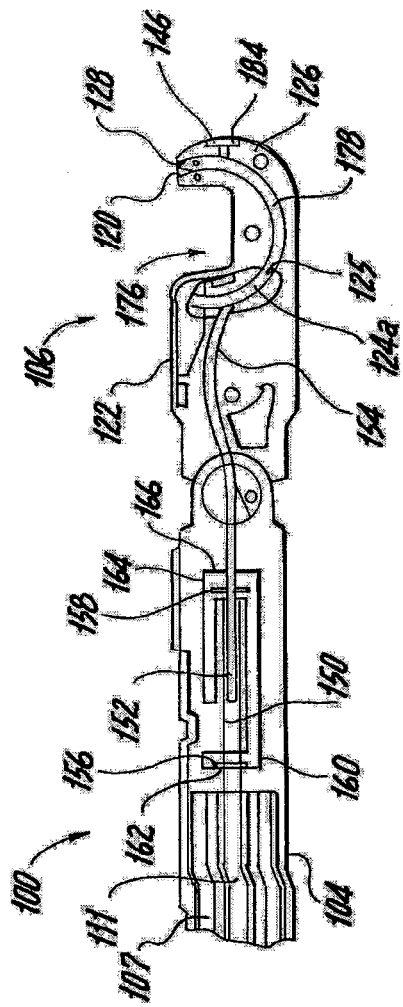
Fig. 1B
Fig. 1C

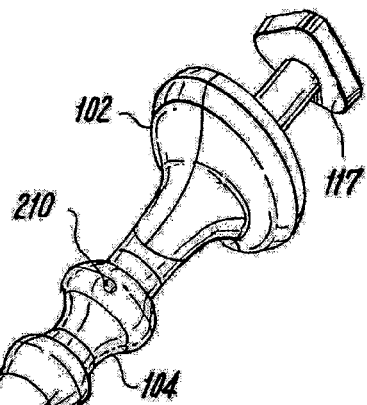
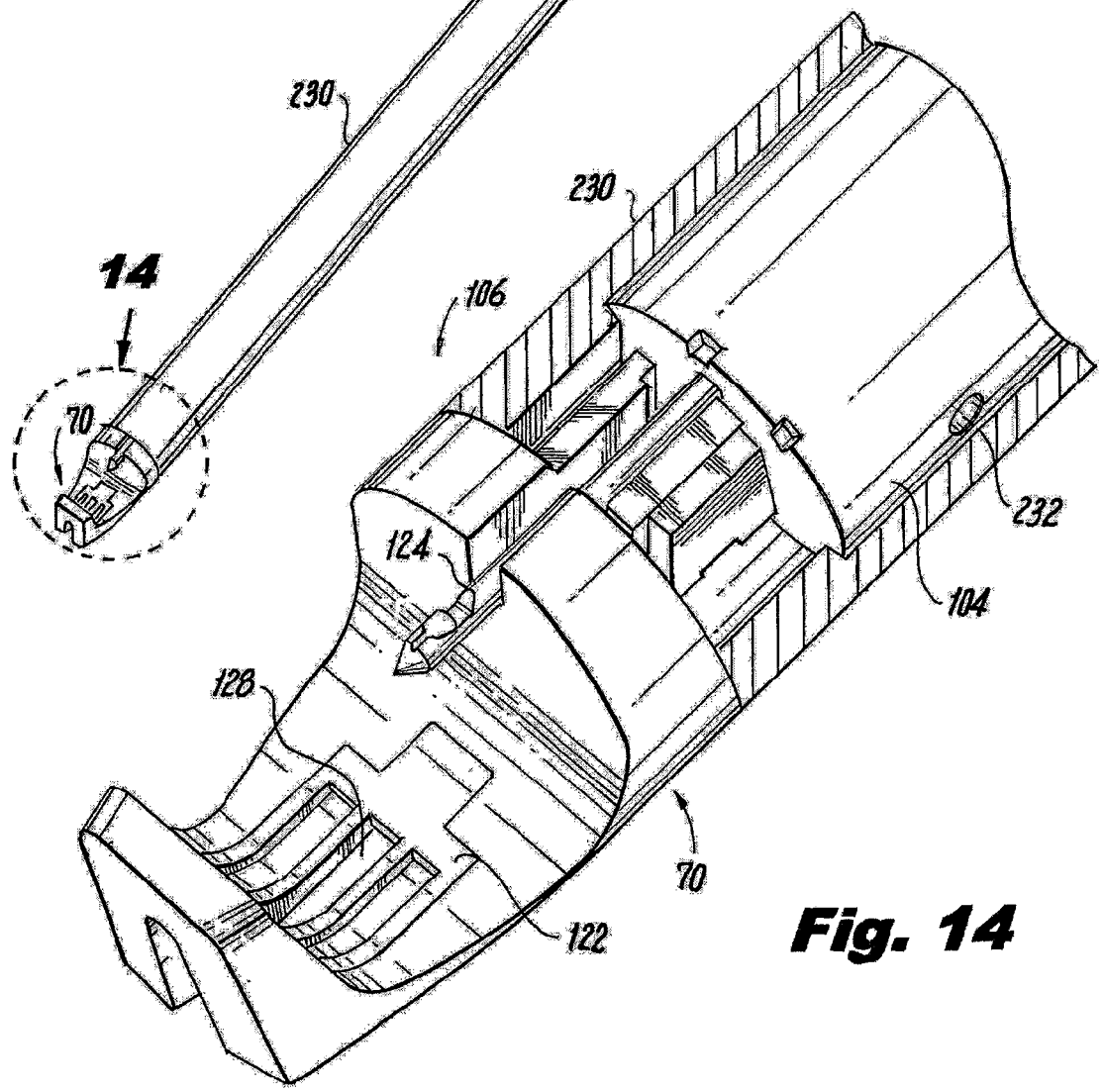
Fig. 13
Fig. 14

PLACING MULTIPLE SUTURES

This application claims priority to U.S. Provisional Patent Application No. 60/851,399, filed Oct. 13, 2006, entitled "Placing Multiple Sutures," the entire content of which is hereby incorporated by reference.

CROSS-REFERENCE TO RELATED CASES

Some related cases naming Michael S. H. Chu as a sole inventor or a co-inventor include: U.S. Pat. No. 6,936,054 and its related U.S. patent application Ser. No. 11/136,805 (published as US 2005/0222589 A1); U.S. Pat. No. 7,122,039; U.S. Pat. No. 7,041,111; pending U.S. patent application Ser. No. 10/921,517 (published as US 2006/0041263 A1); pending U.S. patent application Ser. No. 10/384,682 (published as US 2004/0181243 A1); pending U.S. patent application Ser. No. 10/405,417 (published as US 2004/0199246 A1). Also, some of the subject matter in U.S. Pat. No. 6,955,643 and its related U.S. patent application Ser. No. 11/220,512 (published as US 2006/0004385 A1), both of which name Barry N. Gellman and Jozef Slanda as the two co-inventors, is similar to some of the subject matter herein. The entirety of each of these patents and patent applications is incorporated herein by reference.

TECHNICAL FIELD

The invention generally relates to placing sutures and to navigating tortuous pathways for the purpose of accessing difficult-to-reach treatment areas within the body of a patient.

BACKGROUND INFORMATION

Suturing body tissue is a time consuming aspect of many surgical procedures. For many surgical procedures, it is necessary to make a large opening in the human body to expose the area that requires surgical repair. There are instruments available, such as endoscopes or laparoscopes, that allow viewing of certain areas of the human body through a small puncture wound without exposing the entire body cavity. Endoscopes or laparoscopes can be used in conjunction with specialized surgical instruments to detect, diagnose, and repair areas of the body that previously required open surgery to access.

Some surgical instruments used in endoscopic or laparoscopic procedures are limited by the manner in which they access the areas of the human body in need of repair. In particular, the instruments may not be able to access tissue or organs located deep within the body or that are in some way obstructed. Also, many of the instruments are limited by the way they grasp tissue, apply a suture, or recapture a needle and suture. Furthermore, many of the instruments are complicated and expensive to produce due to the numerous parts and/or subassemblies required to make them function properly.

Suturing instruments, and more specifically suturing instruments used in endoscopic or laparoscopic procedures, are generally rigid and do not provide the operator a range of motion to access difficult-to-reach parts of the anatomical region requiring sutures. Accordingly, multiple instruments of various configurations and sizes typically are used to access all of the necessary tissue areas. These limitations of known suturing instruments complicate endoscopic or laparoscopic procedures for the surgeon by requiring the insertion and removal of multiple instruments from a surgical site as the target suturing area changes during the course of the surgical procedure.

Many medical procedures require that multiple sutures be placed within a patient. Typical suturing instruments enable a surgeon to place only one suture at a time. With such suturing instruments, the surgeon is required to remove the instrument from a surgical site and reload the instrument between placing each suture. Further, the surgeon may be required to use forceps or other instruments to help place the suture. In some instances, the forceps or other instruments may require an additional incision to access the surgical site.

U.S. Pat. No. 5,458,609 discloses a surgical needle and retainer system.

SUMMARY OF THE INVENTION

The invention generally relates to suturing instruments with improved maneuverability, efficiency, and functionality for use during surgical procedures such as endoscopic or laparoscopic procedures. Illustrative embodiments of suturing instruments according to the invention can deliver one or more sutures to a treatment area even when the treatment area is located in a difficult-to-reach area within the body of a patient. (The patient can be a human or other mammal, for example.) Such instruments can transform from a substantially linear instrument to a non-linear instrument by, for example, use of an articulable suturing head that can be positioned straight or at an angle (e.g., up to about 30 degrees) relative to the elongate body of the instrument.

According to one aspect illustrated herein, the invention generally relates to a suturing instrument comprising an elongate body extending from a handle. A suturing head extends from a distal end of the elongate body, and the suturing head is movable relative to the elongate body. Both a first needle carrier and a second needle carrier are movable into and out of the suturing head. Each of the needle carriers can releasably receive a needle with an attached suture, such that two needles can be thrown by the suturing instrument, either simultaneously or one after the other. A first actuator allows controlled movement of the first needle carrier, and this first actuator extends from a proximal end of the handle. A second actuator allows controlled movement of the second needle carrier, and this second actuator also extends from the proximal end of the handle. The suturing head can be articulated and thus movable within a range, for example, of about 0 degrees to about 30 degrees (as measured off of a longitudinal axis running along the length of the elongate body), and this variable articulation angle of the head allows deployment of the first needle carrier and the second needle carrier at various orientations with respect to the longitudinal axis. The first and second needle carriers can be actuated either sequentially or simultaneously. The first needle carrier can receive a first needle to which is attached a first suture. The second needle carrier can receive a second needle to which is attached a second suture. The sutures can be of different colors. Also, the first needle carrier can receive a first needle attached to one end of a suture; and the second needle carrier can receive a second needle attached to the other end of the suture. A further embodiment comprises a needle catch configured to receive a first needle and a second needle, the first needle carrier for receiving the first needle and the second needle carrier for receiving the second needle.

According to another aspect illustrated herein, the invention generally involves a suturing instrument comprising an elongate body member including a handle at a proximal portion. The elongate body can be dimensioned to slidably and rotationally fit within a working channel of an endoscope. The elongate body can also fit and slide within the cannula of a trocar assembly. A cartridge is slidably coupled to the elongate body, and the cartridge includes a needle carrier and at least one needle slot. A needle selection mechanism aligns the needle carrier and the needle slot by rotating the elongate body. An actuator allows movement of the needle carrier toward the needle slot. The needle selection mechanism can comprise a plurality of detents around the elongate body, the plurality of detents engaging the cartridge. There can be three detents around the elongate body, each detent aligning the needle carrier and one of the plurality of needles. The needle carrier can engage a needle in the needle slot to transport the needle from the needle slot to a needle catch.

According to yet another aspect illustrated herein, the invention generally features a suturing instrument comprising an elongate body member including a handle at a proximal portion and a needle carrier at a distal portion. A sheath slidably engages the elongate body, and the sheath includes a plurality of needle slots. A needle selection mechanism aligns the needle carrier of the elongate body and the needle slot of the sheath by rotating the sheath. An actuator allows movement of the needle carrier toward the needle slots. The needle selection mechanism can comprise a plurality of detents around the elongate body, the plurality of detents engaging the sheath. There can be three detents around the elongate body, each detent aligning the needle carrier and one of the plurality of needles. The sheath can rotate clockwise or counterclockwise about the elongate body. The needle carrier can then engage a needle with a suture to transport the needle from the needle slot in the sheath to a needle catch.

BRIEF DESCRIPTION OF THE DRAWINGS

The disclosed embodiments will be further explained with reference to the attached drawings, wherein like structures generally are referenced by like numerals throughout the different drawings. The drawings are not necessarily to scale, the emphasis instead being generally placed upon illustrating the principles of the invention and the disclosed illustrative embodiments.

FIG. 1A shows a perspective view of one embodiment of a suturing instrument in accordance with the invention.

FIG. 1B shows a schematic cross-sectional view of a proximal portion of the suturing instrument of FIG. 1A.

FIG. 1C shows a schematic cross-sectional view of a distal portion of the suturing instrument of FIG. 1A.

FIG. 13 shows an embodiment of a suturing instrument in accordance with the invention having a sheath that rotates about the elongate body of the suturing instrument.

FIG. 14 shows an enlarged view of the suturing instrument of FIG. 13.

DESCRIPTION

Figure 2:
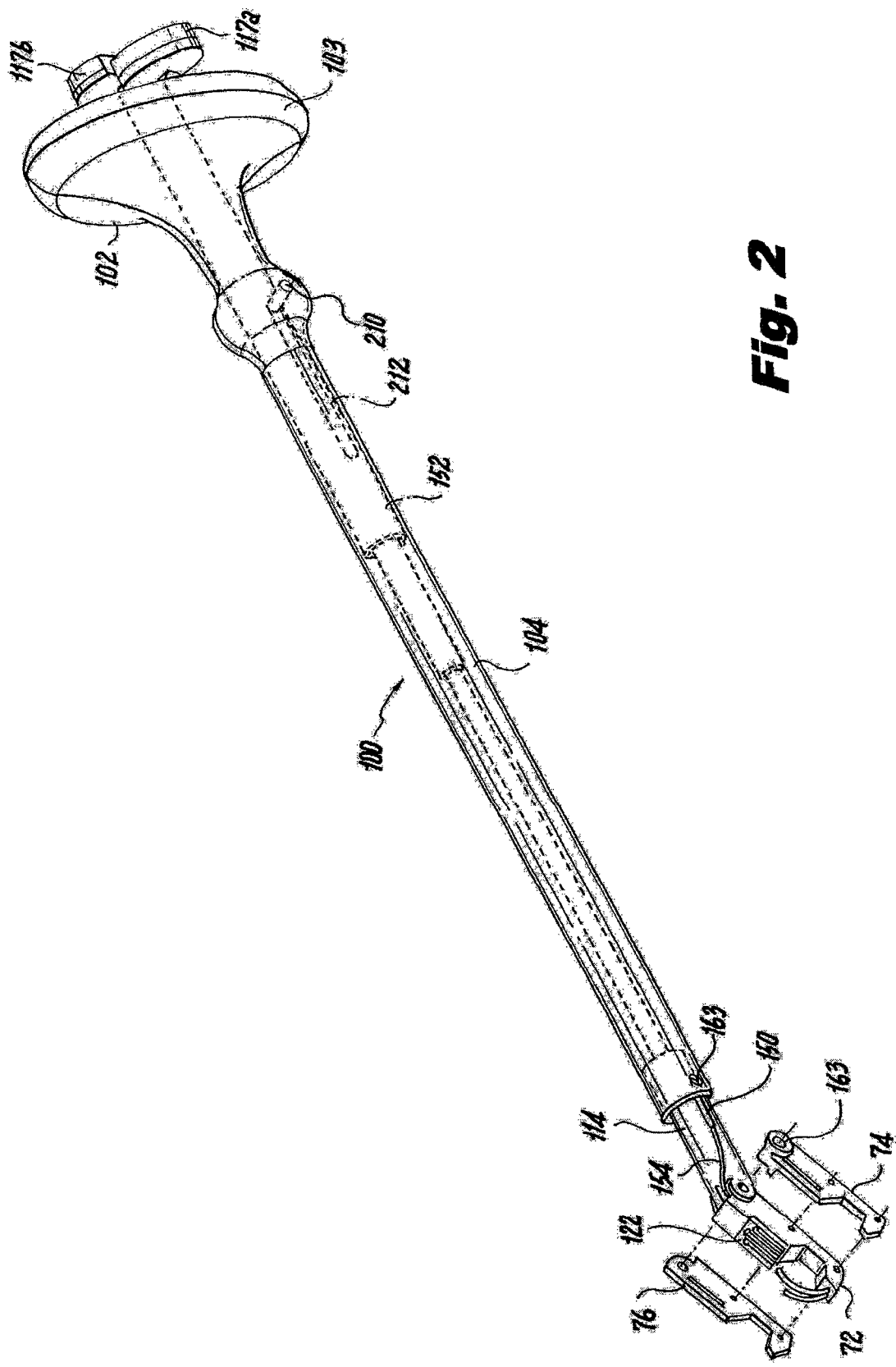
FIG. 2 shows a partial assembly view of one embodiment of a suturing instrument in accordance with the invention.

Illustrative embodiments according to the invention are directed towards a suturing instrument and related methods. The instrument can include a suturing head that is coupled to the shaft of an elongate body member of the instrument by a connector member such that the suturing instrument may pass one or more suture and needle assemblies during a single insertion in a body.

As shown in FIG. 1A, in one embodiment, a suturing instrument 100 includes a handle 102, an elongate body member 104, and a first needle deployment mechanism 110a and a second needle deployment mechanism 110b disposed within the elongate body member 104 and the handle 102. The suturing instrument 100 also includes a distal portion 106 and a proximal portion 108. The elongate body member 104 is mechanically coupled to the handle 102 at the proximal portion 108 and the suturing components are at least partially disposed within the distal portion 106 of the suturing instrument 100.

The handle 102 can take a variety of forms, for example, the handle 102 could be one of the types compatible with suturing systems available from Boston Scientific Corporation of Natick, Mass., in particular with the Capio® Push & Catch suturing system. A suture clip may be coupled to the handle 102 or the elongate body member 104 and used to hold an end of one or more sutures 136 prior to placement in a patient. A plurality of suture slots 103 are located in the handle 102 to manage the sutures and allow for single hand usage. In an embodiment, there are four suture slots 103 spaced about 90 degrees apart on the handle 102. The plurality of suture slots 103 can be used at the discretion of the user.

Generally, the first needle deployment mechanism 110a and the second needle deployment mechanism 110b extend longitudinally through the elongate body member 104 to the distal end 106 of the suturing instrument 100, where the first needle deployment mechanism 110a is coupled to a first needle 128a and the second needle deployment mechanism 110b is coupled to a second needle 128b. The first needle deployment mechanism 110a moves the first needle 128a between a retracted position and a deployed position. The second needle deployment mechanism 110b moves the second needle 128b between a retracted position and a deployed position. One possible needle deployment mechanism is shown in greater detail in FIG. 2 and FIG. 3.

FIG. 1A shows a perspective view of a suturing device 100 with an jointed suturing head 70 that thus is movable. The articulated head 70 also have multiple needle carriers. In the embodiment shown in FIG. 1A, the suturing device 100 has two needle carriers 124a, 124b. Other embodiments could have one, three, four or more needle carriers. The needle carriers 124a, 124b face the same direction. The needle carrier 124a is actuated with an actuator button 117a. The needle carrier 124b is actuated with an actuator button 117b. Depressing a single actuator button 117a, 117b advances the respective needle carriers 124a, 124b. Depressing both actuator buttons 117a, 117b simultaneously advances both needle carriers 124a, 124b at the same time.

Figure 3:
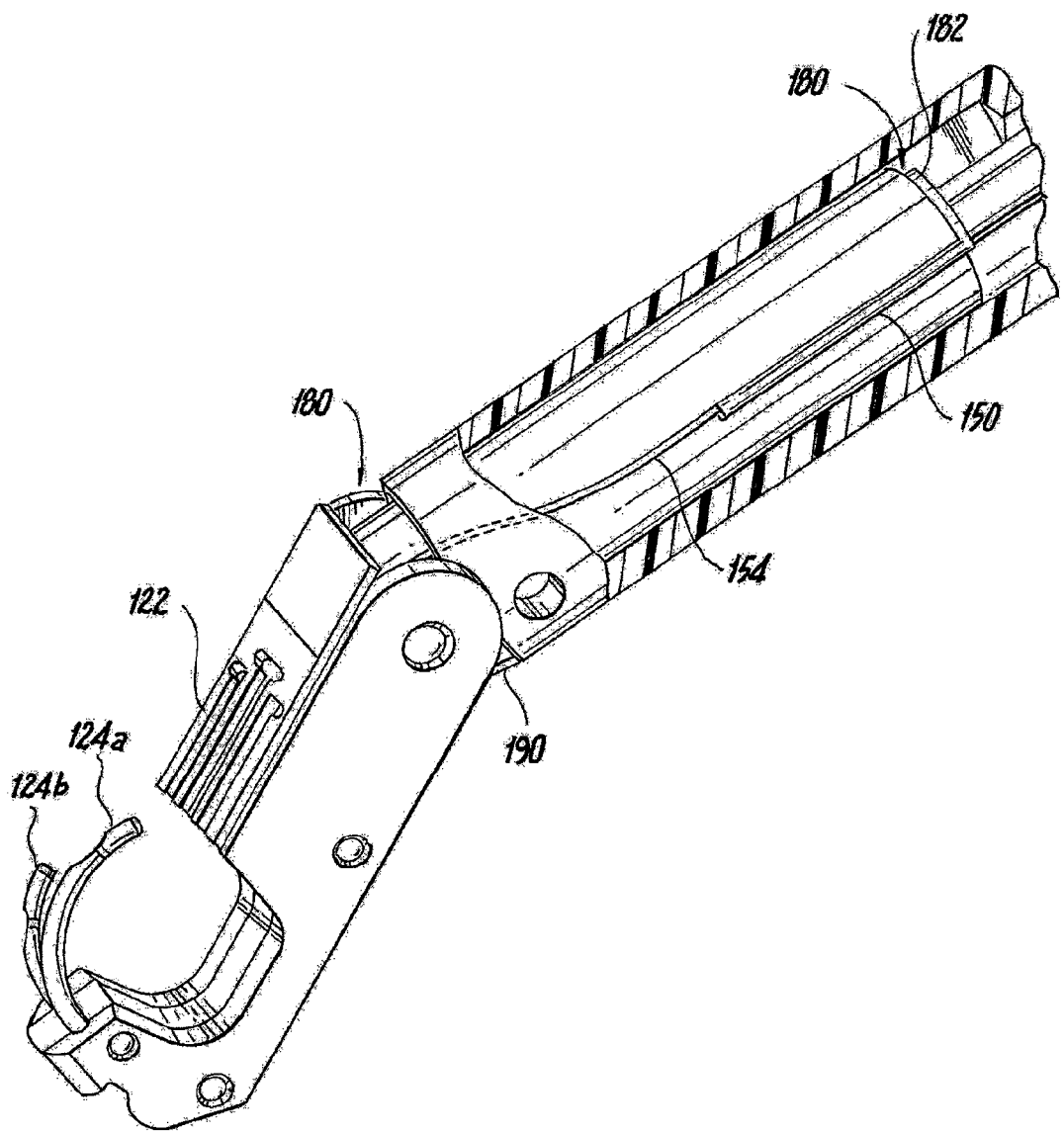
FIG. 3 shows an enlarged view of the suturing head of the suturing instrument of FIG. 1A.

The suturing head 70 can be straightened to slide through an introducer annulus of a trocar. As best shown in FIG. 1 and FIG. 3, the suturing head 70 can be articulated up to 30 degrees or about 30 degrees off of the longitudinal axis of the elongate body, and when at an articulation angle of about 30 degrees a more forward facing carrier bite is possible as opposed to a sideward (that is, about perpendicular to the elongate body's lengthwise longitudinal axis) bite when the suturing head is placed at about zero degrees and essentially straight along the longitudinal axis of the elongate body. By moving the articulated or jointed head off the longitudinal axis of the elongate member, the needle carriers (and thus the needles received by those carriers) can be advanced out of the head in a more forward facing direction. The forward deploying needle carrier can perform multiple sutures in tortuous areas of the body. The forward facing orientation of the suturing head, made possible by the head being jointed or articulated, allows the needles to pass through a larger amount of tissue to form a larger tissue bite. The suturing head 70 being articulable enables the device to reach more difficult locations in the body once the head is disposed within the body of a patient.

The needle carriers 124a, 124b are curved such that when advanced, the needle carriers 124a, 124b will travel in an arc path out of the head and toward the needle catch to obtain a larger tissue bite. The needle carriers 124a, 124b can be the same size in diameter or can be of different diameters to achieve different bite sizes. By having two needles loaded and both needle carriers 124a, 124b facing in the same direction allows the user the opportunity to place two sutures adjacent to each other, at a predetermined distance apart, simultaneously in one needle activation event.

The suturing instrument is adapted for rapid pelvic floor repair by placing multiple sutures in a single insertion near the pelvic floor. Because the suturing head is jointed and can be moved at the joint, the suturing instrument can be used to apply sutures to a wide variety of fixation points within the body of a patient. Multiple sutures can be applied to a single ligament in pelvic floor repair. The suturing instrument can provide multiple sutures for graft fixations, approximate tissue repair, or to ligate vessels in a single insertion.

As shown in FIG. 1B, in one embodiment, the proximal portion 108 of the suturing instrument 100 includes the handle 102, the elongate body member 104, and the needle deployment mechanisms 110a, 110b. The needle deployment mechanism 110a includes the actuator button 117a and a shaft 116 that together form an actuator 112. The needle deployment mechanism 110a also includes a bearing 118 and a button end 119 that defines a hole 121 formed therein. The hole 121 is preferably formed along the central longitudinal axis of the button end 119. The bearing 118 rides along the surface of a lumen 105 that is defined by the inside diameter of the elongate body member 104. A wireform 103 is inserted into the hole 121 of the button end 119, so that the wireform 103 is coupled to the actuator button 117a. A spring 115 encircles the wireform 103, abuts the button end 119, and is compressed between the button end 119 and a spring washer 113. The spring washer 113 is seated upon a center tube 107. The center tube 107 is housed by the lumen 105 and is constrained in the distal portion 106. A pusher wire 111 is attached to the wireform 103 by means of a weld, a coupling, adhesive, or other means, and is slidably disposed within a guidance sleeve 109, the sleeve 109 being disposed within the surface of a lumen 123 defined by the inside diameter of the center tube 107. Similar structures exist in the needle deployment mechanism 110b that are not shown in FIG. 1B.

Referring to FIG. 1C, the distal portion 106 of the elongate body member 104 includes the distal components of the needle deployment mechanism 110a (described in detail below), an operative portion 126, and a needle catch 122. In one embodiment, the operative portion 126 has an arcuate shape and partially encircles a suturing field 176. The operative portion 126 also defines a lumen 178 therein having a needle exit port 120 at an opening into the suturing field 176. The needle 128a is disposed in the needle exit port 120 and is held in place by a slight friction fit. In one embodiment, the suture 136 is attached to the needle 128a. The free end of the suture 136 extends out of the suture slot 146.

Referring again to the needle deployment mechanism 110a, the pusher wire 111 is attached by welding or other means to a coupling 150, which is slidably disposed within a track 152. The coupling 150 is attached to a carrier wire 154, which, by virtue of its attachment to the coupling 150, is also slidably disposed within the track 152. The coupling 150 abuts a backstop washer 156 that is slidably disposed about the pusher wire 111 and is contained within a pocket 114 that includes a back wall 162, against which the backstop washer 156 rests. The track 152 terminates distally in a pocket 164 that includes a wall 166. A downstop washer 158 is slidably disposed about the carrier wire 154 and constrained within the pocket 164.

The carrier wire 154 is mechanically coupled to the extendable needle carrier 124a by welding, coupling, use of adhesives, or by other means. The needle carrier 124a is slidably disposed in the lumen 178 of the operative portion 126 and has a lumen 125 formed at a distal end of the needle carrier 124a. The lumen 125 is dimensioned to releasably receive the non-penetrating end of the needle 128a. The needle carrier 124a is configured to push the needle 128a out of the needle exit port 120 through tissue proximate the suturing field 176, and into the needle catch 122, as will be described in further detail below. In one embodiment, the needle 128a is held within the lumen 125 by a slight friction fit. The operative portion 126 of the distal portion 106 may be pivotable about a pin that is perpendicular to a longitudinal axis 350 of the elongate member 104. Similar structures exist in the needle deployment mechanism 110b that are not shown in FIG. 1C.

In one embodiment, the pusher wire 111 is constructed of an elastic material having "superelastic" properties. Such a material may include alloys of In—Ti, Fe—Mn, Ni—Ti, Ag—Cd, Au—Cd, Au—Cu, Cu—Al—Ni, Cu—Au—Zn, Cu—Zn, Cu—Zn—Al, Cu—Zn—Sn, Cu—Zn—Xe, Fe3Be, Fe3Pt, Ni—Ti—V, Fe—Ni—Ti—Co, and Cu—Sn. In the illustrative embodiment, the superelastic material is a nickel and titanium alloy, commonly known as nitinol available from Memry Corp. of Brookfield, Conn. or SMA Inc. of San Jose, Calif., so chosen for its combination of properties that allow for bendability and high column strength when constrained. The ratio of nickel and titanium in nitinol may vary. One preferred example includes a ratio of about 50% to about 56% nickel by weight. Nitinol also possesses shape retention properties. The pusher wire 111 may also be composed of stainless steel that is annealed for flexibility. The pusher wire 111 is housed in a channel to maintain pushability.

The suture needles are loaded similar to the Capio® Push & Catch suturing system available from Boston Scientific Corporation of Natick, Mass. as described in, for example, co-owned U.S. Pat. No. 6,955,643 issued Oct. 18, 2005, U.S. Pat. No. 6,936,054 issued Aug. 30, 2005, and co-owned pending U.S. patent application Ser. No. 11/136,805, filed on May 24, 2005, the entirety of each of which are incorporated herein by reference. The suture is placed in the front opening of the needle carrier 124a, and the suture is pulled to seat the needle to the needle carrier. The steps are repeated for the second needle carrier 124*b*. The needle carrier can be loaded with one or two suture and needle assemblies or a single suture assembly with two needles at each end. As shown in FIG. 1A, the suturing head 70 is biased towards a substantially non-linear orientation with respect to the elongate body member 104 of the suturing instrument 100. The initial non-linear orientation is possible because a connector member 114 is pre-formed at an angle such that in the absence of an exterior force, the suturing head 70 remains in a substantially non-linear orientation with respect to the elongate body member 104.

FIG. 2 shows a partial assembly view of one embodiment of the suturing instrument 100. The suturing instrument 100 is assembled from multiple components. A pre-determined length of the pusher wire 111 is engaged to a coupling 150 and inserted into a connector hole of the actuator button 117*a* to form a sub assembly. The coupling 150 is an L-shaped tube with an approximately 90 degree bend. Two sub assemblies are then inserted into the elongate body 104 from the proximal portion 108 until the pusher wire 111 extends to the distal portion 106. The spring (not shown in FIG. 2) is loaded over the pusher wire 111 and inserted into the elongate body 104 from the proximal portion 108. The needle carriers 124*a*, 124*b* are then crimped to the distal end of the pusher wire 111. The suture head connector 114 and a push rod 180 (FIG. 3) are inserted into the elongate body 104 from the distal end, while positioning the pusher wire 111 and coupling 150 in their respective tracks along the inside of the elongate body 104, compressing the spring and moving the sub assembly further out the proximal portion 108 of the elongate body 104. The head connector 114 is oval in cross-section, and fits within the shaft of the distal end 106 of the elongated body 104, which has matching but slightly larger cross-sectional oval dimensions. The minor cross-sectional diameter of the head connector 114 is smaller than the diameter of the spring 115, acting as a stop and preventing the spring from advancing further distally in the shaft of the elongated body 104. The pusher wire 111 can be inserted along its tracks in the head connector 114 by depressing buttons 117*a* and 117*b* and compressing the spring 115. A pin or screw is placed in the suture head retaining hole 163 to support and maintain the suture head connector 114.

The suturing head 70 is composed of a suturing core 72 with suturing sides 74 and 76 engaging the suturing core 72. The suturing sides 74 and 76 are assembled on opposite sides of the suturing core in an articulated (about 30 degree) position, with the actuator buttons 117*a*, 117*b* slightly depressed to extend the needle carriers 124*a*, 124*b* slightly forward to position the needle carriers 124*a*, 124*b* and the pusher wire 111 in their respective channels of the suturing head 70. The needle carriers 124*a*, 124*b* are always in tension. A pin or screw through a head connecting hole 78 secures the suturing sides 74 and 76 to the suturing core 72. The screw acts as the axis in which the suturing head 70 pivots. The components of the suturing head 70 are engaged using small rivets, pins, screws or other means of mechanical engagement known to those skilled in the art.

A screw or pin is placed through the elongate body hole 210 and a slot 212 of the actuator buttons 117*a*, 117*b* to align the actuator buttons 117*a*, 117*b* with the elongate body 104 to prevent rotation of the actuator buttons 117*a*, 117*b* relative to the elongate body 104 and limit the travel distance or stroke of the suturing instrument 100. The length of the slot 212 of the actuator buttons 117*a*, 117*b* can vary depending on the size of needle carrier used, for example 10 mm or a 12 mm needle carrier. The slot length of the actuator for the 12 mm carrier should be slightly longer than for the 10 mm carrier due to the longer distance of travel. The stroke travel length can also be adjusted by the length of the connector track in the suture head connector 114 (FIG. 2).

The suturing instrument's component materials should be biocompatible. For example, the handle 102, the elongate body member 104, and portions of the needle deployment mechanisms 110*a*, 110*b* may be fabricated from extruded, molded, or machined plastic material(s), such as polypropylene, polycarbonate, or glass-filled polycarbonate. Other components, for example the needles 128*a*, 128*b*, may be made of metals including stainless steel. Other suitable materials will be apparent to those skilled in the art. The material (s) used to form the suture should be biocompatible. The surgeon will select the length, diameter, and characteristics of the suture to suit a particular application. Additionally, the mechanical components and operation are similar in nature to those disclosed in U.S. Pat. Nos. 5,364,408 and 6,048,351, each of which is incorporated by reference herein in its entirety. The elongate body 104 is preferred to be made in a tubular form instead of two halves to avoid jointing and to provide strength.

FIG. 3 shows an enlarged view of the suturing head 70 of the suturing instrument 100 of FIG. 1A. With the compressed spring (not shown) abutted to a proximal end 182 of the push rod 180 will bias the push rod 180 forward against the suturing head 70 causing the suturing head 70 to articulate to or against a stopping surface 190 to maintain the articulated position of about 30 degrees. Straightening the suturing head 70 will bias the push rod 180 backwards, further compressing the spring. The spring also returns the needle carrier to the retracted position.

The needle catch 122 has a plurality of slots in which the needle can be received. In an embodiment shown in FIG. 3, the needle catch 122 has three slots with a center slot as the preferred target. When both needles are advanced, either needle or both needles can be deflected to an outer slot for acceptance. The needle catch 122 is preferably constructed of thin stainless steel of high temper, such as ANSI 301 full hard. The needle catch 122 may be fabricated by means of stamping, laser machining, or chemical etching.

When using two single needle and suture assemblies, the operation is similar to that of a single carrier device except that the second needle is loaded initially and is available for immediate use without removing the suturing instrument 100 externally for re-loading. The suture can also be color coded to help prevent entanglement when multiple sutures are used. Using different colored sutures allows the user visually track the sutures and avoid twisting or entangling the multiple sutures. For example, the first suture 136 may be clear and the second suture may be blue so the surgeon can differentiate between the sutures during the procedure.

In operation, the user inserts the elongate body member 104 into a patient and orients the elongate body member 104 so that the tissue to be sutured is disposed proximate the suturing field 176 and the needle exit port 120 is proximate to or in contact with the tissue. The user then pushes the actuator button 117*a*. Pushing the actuator button 117*a* causes the needle carrier 124*a* to receive the needle 128*a* in the lumen 125 and then to extend out of the needle exit port 120 and push the needle 128*a* through the tissue. As the first needle 128*a* is pushed through the tissue, the first needle 128*a* pulls the first suture 136 through the tissue. As the user continues to push the actuator button 117*a*, the needle carrier 124*a* continues to advance out of the needle exit port 120 and directs the first needle 128*a* and the first suture 136 toward the needle catch 122. The user continues to push the actuator button 117*a* until the first needle 128*a* contacts and becomes captured by the needle catch 122. The user then retracts the needle carrier 124a by releasing the actuator button 117a. After the user retracts the needle carrier 124a, the first needle 128a and the first suture 136 are left captured within the needle catch 122, with the first suture 136 extending through the tissue.

Pushing the actuator button 117b causes the needle carrier 124b to receive the needle 128b in the lumen 125 and then to extend out of the needle exit port 120 and push the needle 128b through the tissue. As the second needle 128b is pushed through the tissue, the second needle 128b pulls the second suture 136 through the tissue. As the user continues to push the actuator button 117b, the needle carrier 124b continues to advance out of the needle exit port 120 and directs the second needle 128b and the second suture 136 toward the needle catch 122. The user continues to push the actuator button 117b until the second needle 128b contacts and becomes captured by the needle catch 122. The user then retracts the needle carrier 124b by releasing the actuator button 117b. This procedure can be repeated for the third needle, or for as many needles as may be stored in the needle cartridge. After one or more sutures 136 have been placed, the user withdraws the suturing instrument 100 from the patient. The user detaches the suture(s) 136 from the needle(s) 128 and ties a knot or knots in the suture(s) 136. The user can then use the knot pusher 184 to push the knot(s) in the patient as the knot(s) is tightened.

Referring to FIGS. 1A-3, the suturing head 70 of the suturing instrument 100 includes a mechanism for deploying two or more needles 128. The needles 128a, 128b can be deployed sequentially or simultaneously. The deployment mechanism includes a separate needle carrier 124a, 124b for each needle 128a, 128b. The handle 102 can include one actuator button 117a to advance both needles 128a, 128b or the handle 102 can include two buttons 117a, 117b to advance the needles 128a, 128b sequentially or simultaneously (if pressed at the same time). Passing two single armed needles into an incision site enables a user to place, for example, two ligating sutures simultaneously, withdrawing the suturing instrument 100, and tying two knots. Ligating between the sutures is possible in a shorter time-frame.

In operation, for simultaneous advancement, the user advances the needle carriers 124a, 124b by pressing the buttons 117a, 117b until the needles 128a, 128b are driven through the tissue and captured by the needle catch 122. After the needles 128a, 128b are captured in the needle catch 122, the needle carriers 124a, 124b are retracted. For sequential advancement, the user advances one needle carrier 124a by pressing one actuator button 117a until the first needle 128a is driven through the tissue and captured by the needle catch 122. The user then retracts the first needle carrier 124a. The user then advances the second needle carrier 124b by pressing the second actuator button 117b until the second needle 128b is driven through the tissue and captured by the needle catch 122. The user then retracts the second needle carrier 124b.

One benefit of the suturing instrument 100 is a user can create a controlled or predetermined distance between the needle carriers' tissue entrance points. This feature enables the placing of sutures 136 at different spacing sequences. In addition, the suturing instrument 100 also provides a means to place a double-armed suture (a suture with a needle at each end) in a patient.

FIG. 4 through FIG. 9 illustrate the use and stitch of an embodiment of the suturing instrument 100 that has a straight suturing head which does not articulate with respect to the longitudinal axis of the elongate body. The use and stitches shown also apply to the embodiment of the suturing instrument 100 shown in FIGS. 1A-3 with an articulating suturing head 70 with a double needle carrier 124a, 124b. FIG. 4 through FIG. 9 show the use of a double ended needle suture for approximation or anchoring to soft tissue. Having more anchor points spread out in soft tissue distributes the suture load to prevent the suture from tearing or pulling out of the soft tissue.

Figure 4:
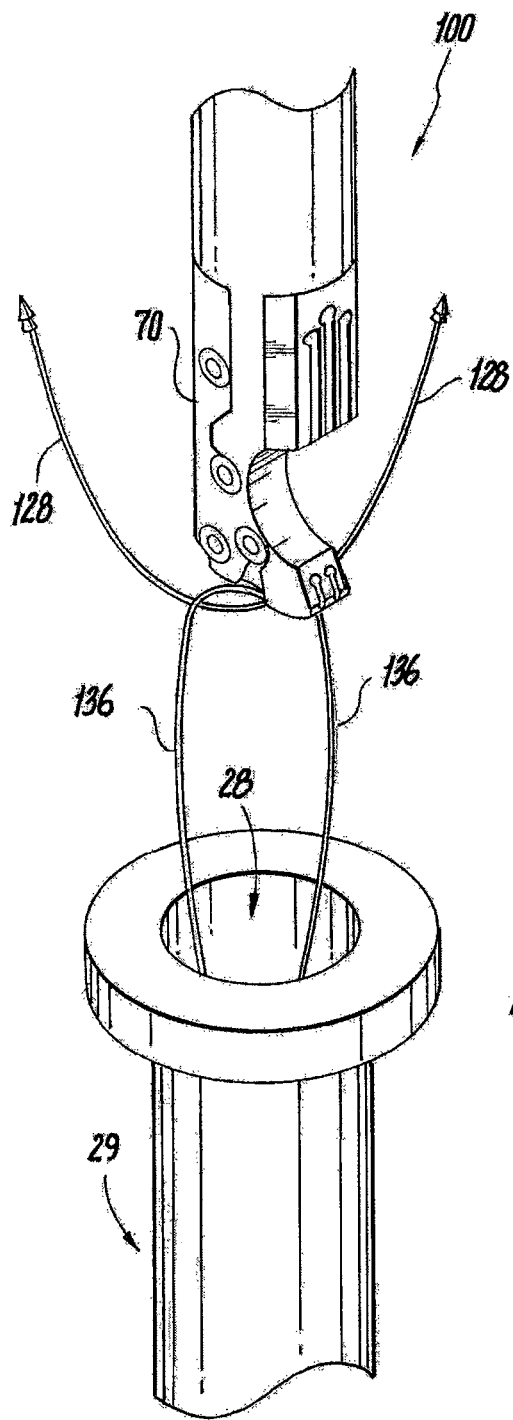
FIG. 4 shows a suturing instrument in accordance with the invention being withdrawn from a cannula of a trocar.

FIG. 4 shows the suturing instrument 100 being withdrawn from a cannula 28 of a trocar 29. The suturing instrument 100 is working through the cannula 28 after both needles have been placed through tissue and withdrawn externally through the cannula 28. A knot is then pushed down using the knot pusher located in the front of the suturing instrument 100. By using a single suture with a needle on both ends reduces the knot procedure in half and prevents the sutures from entanglement versus using two single needle sutures. Use of two single needle sutures would require two knots and four sutures exiting the cannula. Open access procedures would have fewer problems with suture management by using a single suture with a needle on both ends.

The trocar 29 produces an external force on the connector member 114 which substantially straightens the connector member 114 thereby resulting in a substantially linear relationship between the suturing head 70 and the elongate body member 104.

In an embodiment, the trocar 29 comprises a biocompatible plastic. In an embodiment, the trocar 29 comprises a biocompatible polymer. In an embodiment, the trocar 29 is a laparoscopic trocar 29. The trocar 29 comprises a material capable of supplying an external force on the suturing instrument 100 which results in a substantially linear relationship between the suturing head 70 and the elongate body member 104 of the suturing instrument 100. Therefore, the suturing instrument 100 surrounded by the trocar 29 may be delivered to the treatment area while maintaining a substantially linear relationship between the suturing head 70 and the elongate body member 104.

Figure 5:
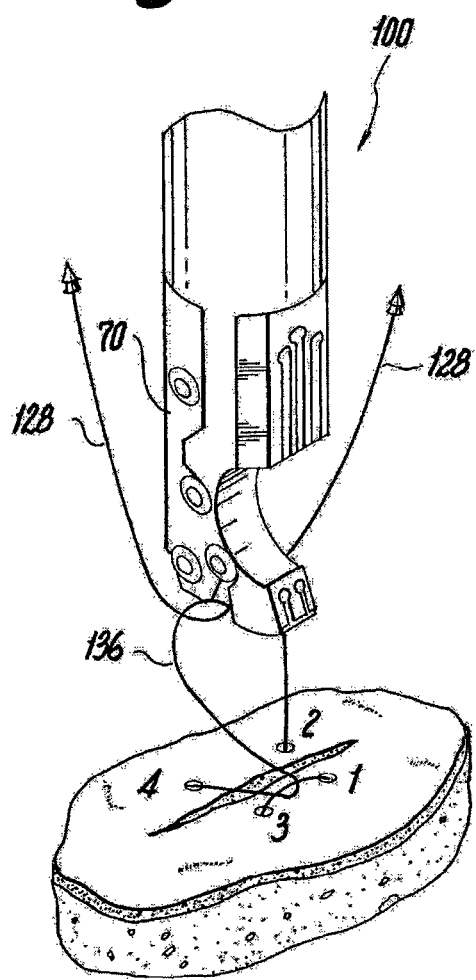
FIG. 5 shows a suturing instrument in accordance with the invention forming a suture having a "K" suture pattern.

FIG. 5 shows the suturing instrument 100 forming a suture having a "K" suture pattern. The first needle 128a is placed from point 1 to point 2 and the second needle 128b is placed from point 3 to point 4. The suturing instrument 100 is removed external to the body where the needles 128a, 128b are removed from the needle catch 122. The end of one suture 136 is slipped around the loop between point 1 and 3. The ends of the sutures 136 are pulled until the loop between point 1 and 3 is taunt. The suture ends are wrapped around each other and pushed down with the knot pusher to form the first portion of the knot. A second wrapping of the suture ends is pushed downward to complete the knot.

Without cutting off the needles 128a, 128b, the needles 128a, 128b can be re-loaded onto the double needle carrier again to form a double suture bridge within the body for suspension or approximation. The suture bridge supports the suture from engagement with the incision and is formed with multiple sutures. The suture bridge can be parallel or form a triangular bridge with sutures branching off in different directions.

Figure 6:
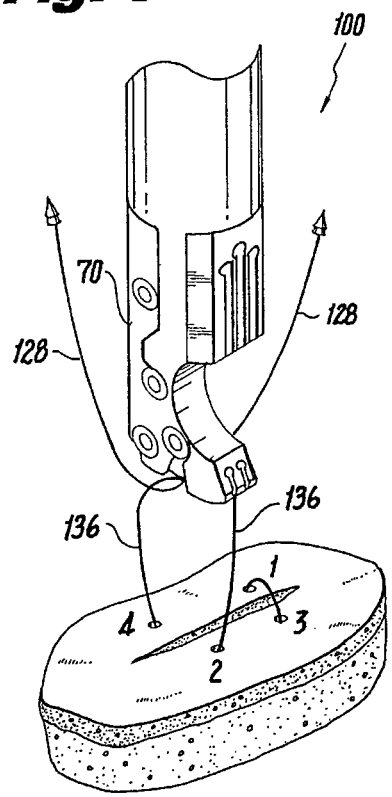
FIG. 6 shows a suturing instrument in accordance with the invention forming a suture having a parallel suture pattern.

FIG. 6 shows the suturing instrument 100 forming a suture having a parallel suture pattern where the first needle 128a is placed from point 1 to point 2 and the second needle 128b is placed from point 3 to point 4. The suturing instrument 100 is removed external to the body where the needles 128a, 128b are removed from the needle catch 122. The suture ends are wrapped around each other and are pushed down with the knot pusher to form the first portion of the knot. A second wrapping of the suture ends is pushed downward to complete the knot.

Figure 7:
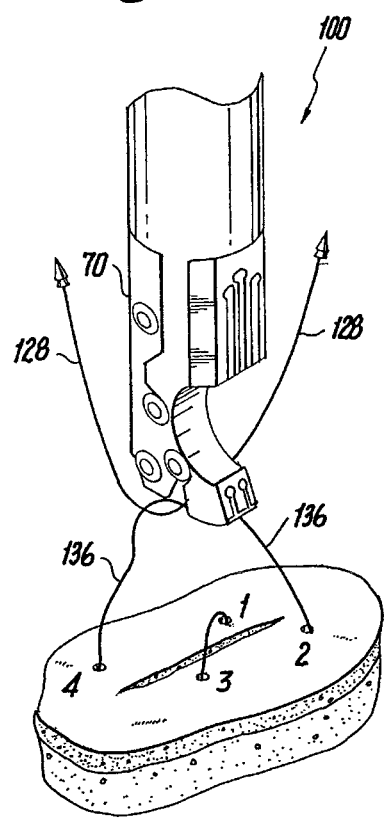
FIG. 7 shows a suturing instrument in accordance with the invention forming a suture having an "X" suture pattern.

FIG. 7 shows the suturing instrument 100 forming a suture having an "X" suture where the first needle is placed from point 1 to point 2 and the second needle is placed from point 3 to point 4. The suturing instrument 100 is removed external to the body, the needles 128a, 128b are removed from the needle catch 122. The suture ends are wrapped around each other and are pushed down with the knot pusher to form the first portion of the knot. A second wrapping of the suture ends is pushed downward to complete the knot.

Figure 8:
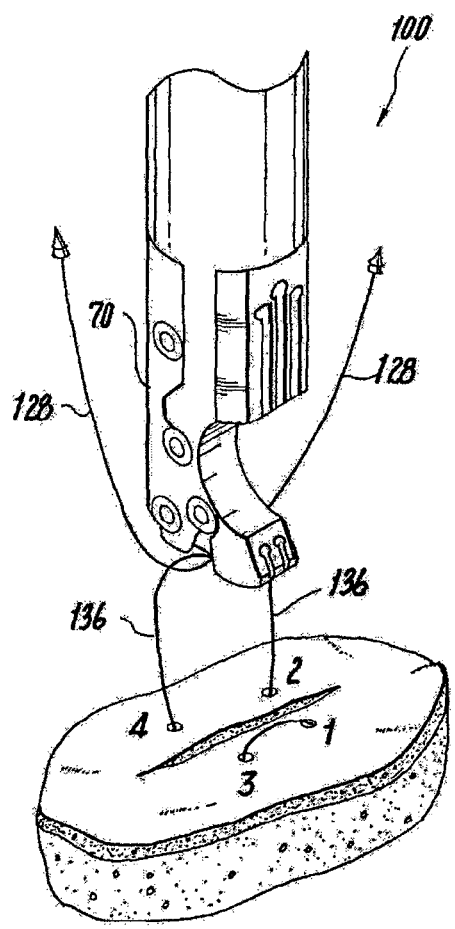
FIG. 8 shows a suturing instrument in accordance with the invention forming a suture having an underneath "X" suture pattern.

FIG. 8 shows the suturing instrument 100 forming a suture having an underneath "X" suture pattern where the first needle 128a is placed from point 1 to point 2 and the second needle 128b is placed from point 3 to point 4. The suturing instrument 100 is removed external to the body, the needles 128a, 128b are removed from the needle catch 122. The suture ends are wrapped around each other and are pushed down with the knot pusher to form the first portion of the knot. A second wrapping of the suture ends is pushed downward to complete the knot.

Figure 9:
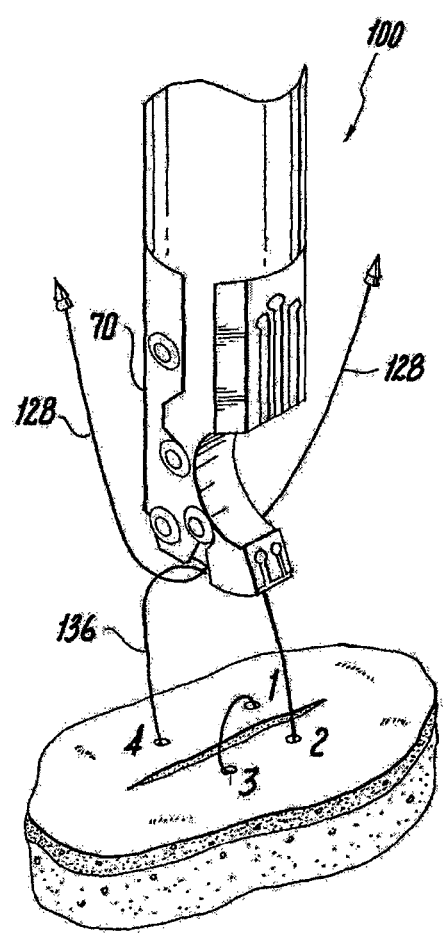
FIG. 9 shows a suturing instrument in accordance with the invention forming a suture having a large "X" suture pattern.

FIG. 9 shows the suturing instrument 100 forming a suture having a large "X" suture pattern similar to FIG. 7 except that the suturing head 70 is angled more (obtuse) where the first needle 128a is placed from point 1 to point 2 and the second needle 128b is placed from point 3 to point 4. The suturing instrument 100 is removed external to the body, the needles 128a, 128b are removed from the needle catch 122. The suture ends are wrapped around each other and are pushed down with the knot pusher to form the first portion of the knot. A second wrapping of the suture ends is pushed downward to complete the knot.

Figure 10:
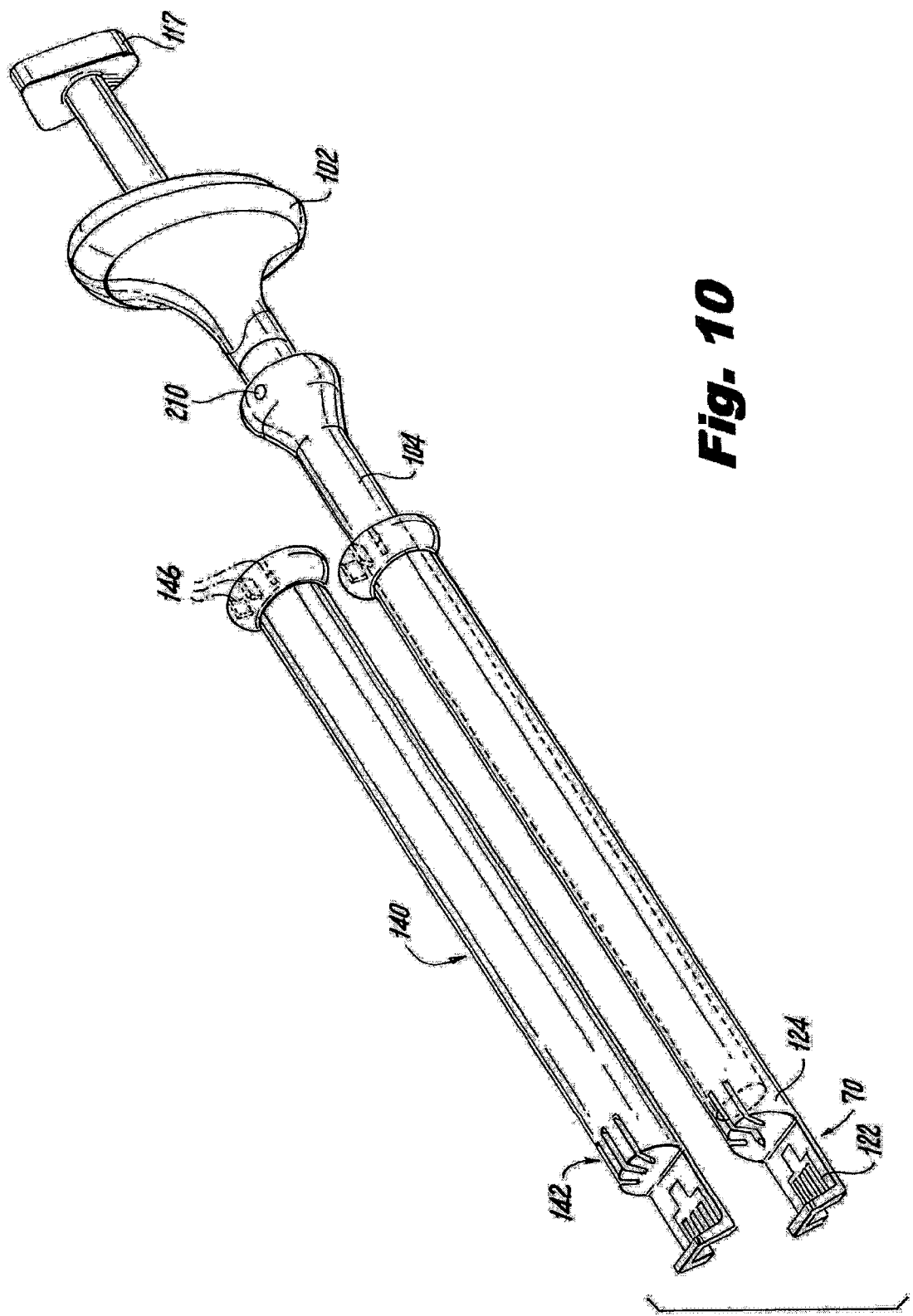
FIG. 10 shows one embodiment of a suturing instrument in accordance with the invention having multiple needle and suture assemblies.

FIG. 10 shows an alternative embodiment of a suturing instrument having multiple needle and suture assemblies. A suturing instrument comprises an elongate body member 104 including a handle 102 at a proximal portion; a cartridge 140 slidably coupled to the elongate body 104, the cartridge 140 containing a needle carrier 124 and a plurality of needles; a needle selection mechanism that aligns the needle carrier 124 and the needle to be transported by rotating the elongate body 104; and an actuator 117 for coupling the needle carrier 124 to the needle to transport the needle from the cartridge 140 to a needle catch 122. This embodiment has exchangeable and disposable cartridges with needle and suture assemblies preloaded in the needle slot and the respective suture managed in the suture slot.

Figure 11:
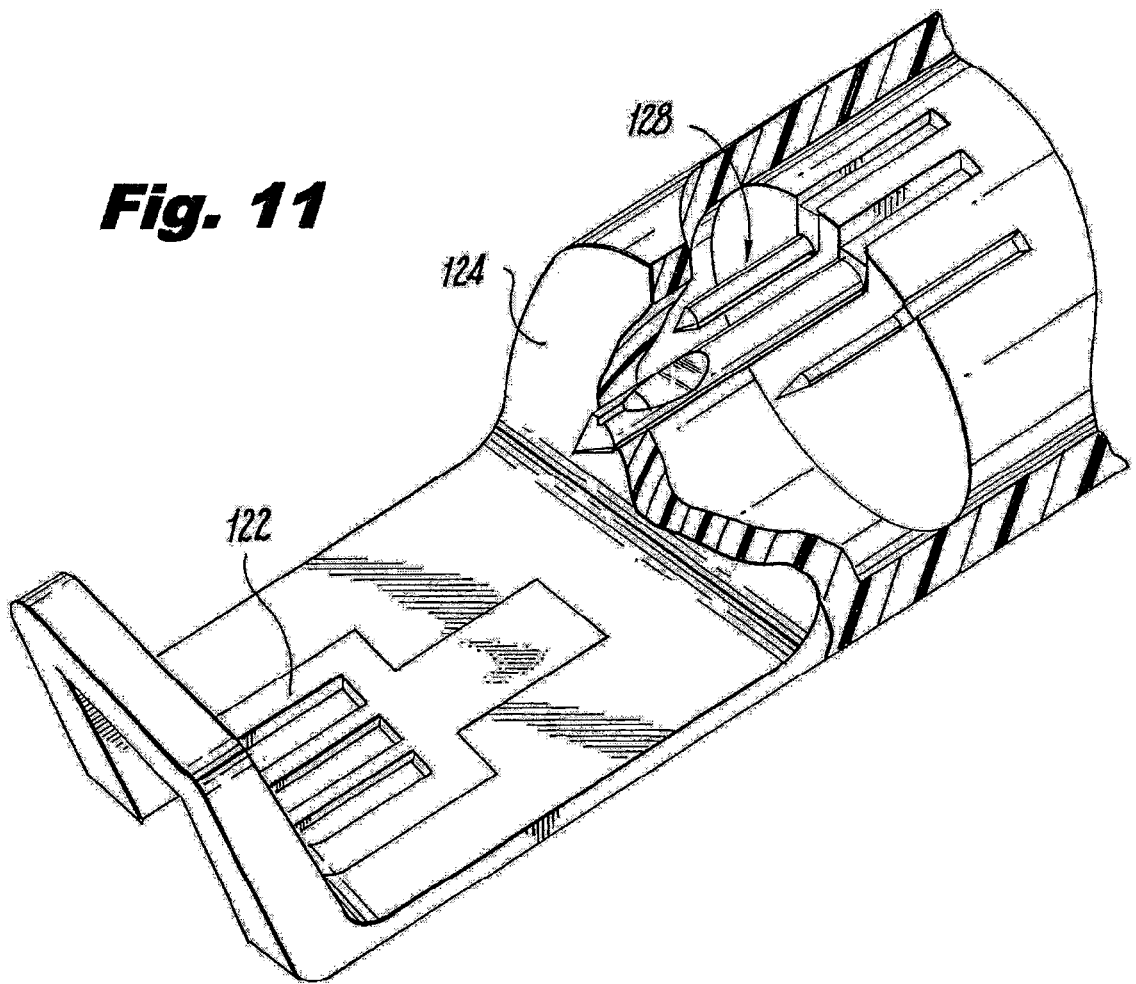
FIG. 11 shows an enlarged view the suturing instrument of FIG. 10 having multiple needle and suture assemblies.

FIG. 11 shows an enlarged view the suturing instrument of FIG. 10 having multiple needle and suture assemblies. The needle slots 142 are oriented radially to be aligned to the single straight carrier of the elongate body when coupled. The elongate body 104 consists of a single piece L-shaped carrier 124 which connects to the hole of the actuator button 117 similar to the embodiments shown in FIGS. 1A-3. A spring (not shown) between the front wall of the elongate body 104 and the front end of the actuator button 117 biases the actuator button to extend out from the back end of the elongate body and returns the carrier to the retracted position just behind the front wall of the elongate body 104. A pin or screw in the elongate body hole 210 and the slot 212 of the actuator 117 limits the stroke length.

One circle path and three detents (not shown) around the elongate body allows the cartridge to couple or snap to the elongate body 104. The detent aligns the carrier 124 of the elongate body 104 to one of the three needle slots of the carrier 124. The elongate body can rotate clockwise or counter clockwise within the cartridge 140. The user may prefer to place the needles in any order or may elect to start with the outer most needle, then index to the next consecutive needle.

In operation, this alternative embodiment functions largely the same way as the embodiment previously described. The pre-loaded cartridge 140 is slid on to couple to the elongate body 104. The mouth of the carrier is positioned to the desired location. The needle 128 is selected by rotating the elongate body 104 to the detent, aligning the carrier 124 to the needle 128. The actuator button 117 is depressed, coupling the carrier 124 to the needle 128 as the carrier 124 is advanced to transport the needle 128 with the suture 136 through tissue. The needle catch 122 receives the needle 128. The spring returns the carrier 124 to the retracted position. The caught needle 128 can be removed external to the body or the elongate body is rotated to another selected needle for deployment at the same location or at a different location.

Alternatively, other mechanisms could be used to advance the needles 128 from the needle cartridge 140 to the carrier 124. In one embodiment, the needles 128 in the needle cartridge 140 are held in a loading slot by a friction fit and are pushed into an exit aperture when a needle push plate is activated by the user. For example, instead of a spring, a dispensing control rod coupled to an actuator button on the handle 102 and the push plate may be provided. Alternatively, a spring release mechanism coupled to the spring and an actuator button on the handle 102 may be provided to enable the user to release the spring so that the push plate loads the needles 128 into the exit aperture to be received in the lumen 125 of the needle carrier 124. In another embodiment, the user may load the needles 128 into the exit aperture by pulling the free end of the suture 136. In yet another embodiment, the suturing instrument 100 may include a means for pulling the free end of the suture 136 such as, for example, a spool or a lever attached to the elongate body member and disposed, for example, on or within the handle 102.

Figure 12:
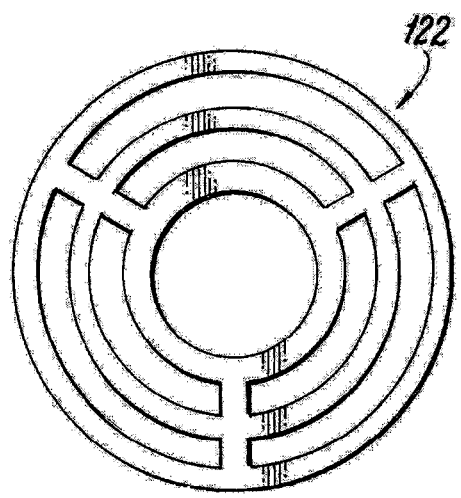
FIG. 12 shows a needle catch for receiving suture needles.

FIG. 10 and FIG. 11 have three needles per cartridge 140 to correspond to the three needle slots of the needle catch 122. FIG. 12 shows a needle catch 122 for receiving multiple suture needles. The needle catch 122 of FIG. 12 allows more suture needles to be placed around the radius of the cartridge such that the needle catch will receive the needles. This embodiment of the needle catch 122 accepts multiple types of needle and suture assemblies known in the art.

FIG. 13 shows an alternative embodiment of a suturing instrument 100 where a sheath 230 containing multiple needle and suture assemblies rotates about the elongate body 104. A suturing instrument 100 comprises an elongate body member 104 including a handle 102 at a proximal portion and a needle carrier 124 at a distal portion; a sheath 230 slidably engaging the elongate body 104, the sheath 230 containing a plurality of needles 128; a needle selection mechanism that aligns the needle to be transported and a needle carrier 124 by rotating the sheath 230; and an actuator for coupling the needle carrier 124 to the needle 128 to transport the needle from the sheath 230 to a needle catch 122. This embodiment has a sheath 230 with needle slots which the user or the manufacturer can pre-load with needles and suture assemblies and the respective suture managed in the suture slots.

FIG. 14 shows an enlarged view of the distal end 106 of the suturing instrument 100 of FIG. 13. The needle slots are oriented radially and alignable to the single straight carrier. The elongate body 104 houses a single piece L-shaped carrier which connects to the hole of the actuator button 117 similar to the embodiments shown in FIGS. 1A-3. A spring (not shown) between the front wall of the elongate body 104 and the front end of the actuator button 117 bias the actuator button 117 to extend out from the back end of the elongate body 104 and return the carrier 124 to the retracted position just behind the front wall of the elongate body 104. A pin or screw in the elongate body hole 210 and the slot 212 of the actuator button 117 limits the stroke.

The sheath 230 is assembled by sliding it onto the elongate body 104, then the head is secured to the elongate body by a pin or screw in the distal shaft hole 232. The screw is placed through a hole in the sheath (not shown). Multiple detents (not shown) around the elongate body 104 allows the sheath 230 to align the carrier 124 to one of the multiple needle slots. The needle slot is sized to fit the needle diameter and has a clearance slot for the suture to exit (suture not shown).

The sheath 230 can rotate clockwise or counter clockwise about the elongate body 104. The user may prefer to place or use the needles in any order or may elect to start with the needle furthest and index to the next consecutive needle. The sheath 230 can be made to index or rotate to the next needle by the activation or depression of the same actuator button to advance the carrier such that the needle indexing is automated.

In operation, this alternative embodiment functions largely the same way as the embodiments previously described. The sheath 230 is preloaded by the user (or manufacturer). The mouth is positioned at the desired location. The needle 128 is selected by rotating the sheath 230 to the detent, aligning the carrier 124 to the needle 128. The actuator 117 is depressed to couple the carrier 124 to the needle 128 as the carrier 124 transports the needle 128 with the suture 136 through tissue. The needle catch 122 receives the needle 128. The spring returns the carrier 124 to the retracted position. The caught needle can be removed external to the body or the sheath 230 is rotated to another selected needle for deployment at the same location or at a different location (without removing the device for reloading).

Certain embodiments according to the invention have been disclosed. These embodiments are illustrative of, and not limiting on, the invention. Other embodiments, as well as various modifications and combinations of the disclosed embodiments, are possible and are within the scope of this disclosure.

What is claimed is:

1. A suturing instrument, comprising:
   an elongate body extending from a handle, the elongate body defining a longitudinal axis and comprising a proximal end and a distal end, the elongate body also comprising a spring and a push rod;
   a suturing head extending from the distal end of the elongate body, the suturing head configured to, in the presence of a force external to the suturing head, be substantially aligned along the longitudinal axis such that the suturing instrument is in a linear configuration, and, in the absence of the force external to the suturing head, be articulated from the longitudinal axis such that the suturing instrument is in a non-linear configuration, the spring and the push rod of the elongate body being operably associated with the suturing head so as to articulate the suturing head from the longitudinal axis in the absence of the force external to the suturing head;
   a first needle carrier and a second needle carrier, both being movable into and out of the suturing head;
   a first actuator for controlling movement of the first needle carrier, the first actuator extending from a proximal end of the handle; and
   a second actuator for controlling movement of the second needle carrier, the second actuator extending from the proximal end of the handle; the first and second actuators configured such that depression of the first actuator or the second actuator causes deployment of the first needle carrier or the second needle carrier, respectively, and also compression of the spring and movement of the push rod.

2. The suturing instrument of claim 1 wherein the suturing head is movable within an articulation angle range of about 0 degrees to about 30 degrees off of an axis perpendicular to the longitudinal axis of the elongate body.

3. The suturing instrument of claim 2 wherein the articulation angle of the suturing head relative to the elongate body enables deployment of the first needle carrier and the second needle carrier at various orientations with respect to the longitudinal axis.

4. The suturing instrument of claim 1 wherein the first needle carrier and the second needle carrier are actuated either sequentially or simultaneously.

5. The suturing instrument of claim 1 further comprising a first suture attached to a first needle and a second suture attached to a second needle, the first needle carrier for receiving the first needle, the second needle carrier for receiving the second needle.

6. The suturing instrument of claim 5 wherein the first and second sutures are of different colors.

7. The suturing instrument of claim 1 further comprising a suture having a first end attached to a first needle and a second end attached to a second needle, the first needle carrier for receiving the first needle and the second needle carrier for receiving the second needle.

8. The suturing instrument of claim 1 wherein the elongate body is dimensioned to slidably and rotationally fit within a working channel of an endoscope.

9. The suturing instrument of claim 1 further comprising a needle catch configured to receive a first needle and a second needle from the first needle carrier and the second needle carrier, the first needle carrier for carrying the first needle and the second needle carrier for carrying the second needle.

10. The suturing instrument of claim 1 further comprising a trocar surrounding a length of the suturing instrument.

11. A suturing instrument, comprising:
    a handle;
    an elongate body extending from the handle along a longitudinal axis, the elongate body having a proximal end and a distal end;
    a spring disposed within the elongate body;
    a suturing head pivotably coupled with the distal end of the elongate body, the suturing head being operably coupled with the spring such that:
       aligning the suturing head substantially along the longitudinal axis, in response to a force external to the suturing head, compresses the spring; and
       decompression of the spring articulates the suturing head from substantial alignment with the longitudinal axis;
    a needle carrier movable into and out of the suturing head;
    an actuator configured to control movement of the needle carrier, the actuator extending from a proximal end of the handle.

12. The suturing instrument of claim 11, wherein:
    depression of the actuator causes deployment of the needle carrier and compression of the spring; and
    release of the actuator causes decompression of the spring and retraction of the needle carrier.

13. The suturing instrument of claim 11, further comprising a stopping surface disposed at the distal end of the elongate body, the stopping surface being configured to maintain an articulated position of the suturing head.

14. The suturing instrument of claim 11, further comprising a needle disposed within the needle carrier.

15. The suturing instrument of claim 11, further comprising a push rod disposed between the suturing head and the spring, the push rod being configured to bias the suturing head to an articulated position and compress the spring in response to the suturing head being aligned along the longitudinal axis.

* * * * *